United States Patent [19]

Nadeau

[11] 4,070,493
[45] Jan. 24, 1978

[54] DIAGNOSTIC KIT

[75] Inventor: Jacques A. Nadeau, Laurent, Canada

[73] Assignee: Merck & Co., Inc., Rahway, N.J.

[21] Appl. No.: 778,207

[22] Filed: Mar. 16, 1977

[51] Int. Cl.$^2$ .................. A61K 29/00; A61K 43/00
[52] U.S. Cl. ........................................ 424/1; 23/259; 424/9; 252/311
[58] Field of Search ............... 252/311; 424/1, 9

[56] References Cited

U.S. PATENT DOCUMENTS

| 3,875,299 | 4/1975 | Winchell et al. | 424/1 |
|---|---|---|---|
| 3,992,513 | 11/1976 | Petkau et al. | 424/1 |

OTHER PUBLICATIONS

Aburano et al., Life Sciences, vol. 12, June 30, 1975, Abstract No. 3, 33622, p. 3371.
Columbetti, Radiobiol.—Radiother., Jan., 1974, pp. 47–51.
Johnson et al., J. of Nuclear Medicine, vol. 11, No. 1 (1970), pp. 564–565.
Sewakar et al., Nuclear Medicine, vol. XIV, No. 1, Mar. 31, 1975, pp. 46–51.
Subramanian et al. J. of Nucl. Med., vol. 11, No. 6, 1970, pp. 365–366.
Subramanian et al., J. of Nucl. Med., vol. 14, No. 6, 1973, p. 459.

*Primary Examiner*—Benjamin R. Padgett
*Assistant Examiner*—Christine M. Nucker
*Attorney, Agent, or Firm*—Thomas E. Arther; Harry E. Westlake, Jr.; Rudolph J. Anderson, Jr.

[57] ABSTRACT

This invention relates to a colloid-forming composition useful in medical diagnosis. More particularly, it relates to an improved kit useful as a diagnostic aid comprising colloid-forming reagent solutions.

It further relates to a kit useful in medical diagnosis which comprises in combination a lyophilized Stannous-phytate complex and a buffered calcium chloride solution.

5 Claims, No Drawings

DIAGNOSTIC KIT

BACKGROUND OF THE INVENTION

Other methods are disclosed in the literature or are in commercial use which provide diagnostic compositions of Technetium Tc 99m suitable for imaging liver but which have certain aspects limiting their usefulness.

One such method employs an injectable solution of Technetium 99m present as the pertechnate ion, complexed with sodium phytate. Although this composition provides a method for imaging liver, it is unsatisfactory for imaging the spleen and bone marrow.

Another such preparation for use in diagnosis is known as a Technetium Tc 99m sulfur colloid. Although compositions of this type are useful for imaging spleen and bone marrow as well as liver, they are tedious and time consuming for the clinician to employ. Since the injectable sulfur colloid must be freshly prepared, the person who carries out the procedure must carry out a series of time-consuming steps including addition of pertechnate solution, acidification, heating the solution, further pH adjustment, cooling, and allowing to stand for a period of time. This lengthy procedure is an inherent disadvantage in the use of such Technetium 99m Sulfur Colloids.

SUMMARY OF THE PRESENT INVENTION

In accordance with the present invention, there is provided a diagnostic kit suitable for use in imaging liver, spleen, and bone marrow. The kit, ordinarily containing sufficient material for more than one dose, comprises two containers, one of which contains a freeze-dried mixture of a water-soluble salt of phytic acid and a non-toxic stannous compound, the other of which contains a buffered aqueous solution of a non-toxic calcium compound wherein the said soluble salt of phytic acid and said non-toxic calcium compound are present in a ratio of approximately 1:1 parts by weight. The first of said containers preferably contains a freeze-dried mixture of 10 mg. (9–11 mg.) of sodium phytate and stannous chloride added as 1 mg. (0.5–1.1 mg.) of stannous chloride dihydrate. The second of said containers contains a solution of a soluble calcium salt, preferably 12.5 mg. (10–15 mg.) of calcium chloride dihydrate preferably buffered with 12.5 mg. (10–15 mg.) of potassium biphthalate in 2.5 ml. of normal saline solution. This provides approximately 10 mg. of calcium chloride dihydrate/10 ml. of solution.

In the process of preparing the instant diagnostic kit, it is essential that the two vials be prepared observing aseptic techniques and using normal saline solution as the diluent so that the two ingredients are compatible and may be intravenously injected without further treatment after mixing. Another important feature of the present invention is the ratio of amounts of the phytate salt of reagent No. 1 and the calcium salt of reagent No. 2. It is important to the present invention that the weight ratio of phytate salt to calcium salt is about 1:1. In preparing the components of the present kit, the first component is prepared by dissolving ten parts by weight of sodium phytate and one part by weight of stannous chloride dihydrate in water made slightly acid with hydrochloric acid and diluting with water to a concentration of approximately 0.1 to 1% of sodium phytate by weight, subdividing the bulk solution into individual dosage amounts and aseptically freeze drying the individual dosages to provide a readily-soluble mixture of 10 mg. sodium phytate and 1 mg. stannous chloride. The second component of the kit is prepared by dissolving equal parts by weight of calcium chloride dihydrate and potassium biphthalate in water, adjusting the pH to approximately 3.2 using hydrochloric acid and sodium hydroxide solution and diluting the mixture with water to a concentration of approximately 0.5% calcium chloride by weight. The bulk solution is then aseptically subdivided into individual vials of solution containing 12.5 mg. of calcium chloride per vial.

The kit comprising component 1 and component 2 is readily employed as a diagnostic tool for imaging liver, spleen, and bone marrow in the following manner. To the freeze-dried mixture of sodium phytate and stannous chloride is added a solution of 2–8 ml. of a solution containing approximately 20–50 millicuries of sodium pertechnate Tc 99m. An injectable colloid of calcium phytate labeled with Tc 99m is formed by the addition of the buffered calcium chloride solution to the sodium phytate-pertechnate mixture described above. This radioactive colloid can be injected immediately without further treatment.

In utilizing the instant kit for imaging liver, spleen, and bone marrow, an aqueous solution of from 2–8 milliliters of the required amount of sodium pertechnate $Tc^{99m}$ (available as instant Technetium$^{99m}$ or from a sterile generator of the type described in U.S. Patent 3,369,121) is mixed with the lyophilized mixture of sodium phytate and stannous chloride to form a solution of reduced pertechnate ion bound to phytate. This solution is then aseptically mixed with the buffered calcium chloride solution to form a calcium phytate $Tc^{99m}$ colloid immediately ready for injection into the patient. Unlike the prior art sodium phytate pertechnate solution, which is primarily useful in imaging the liver, the present kit effectively images not only the liver but also the spleen and the bone marrow of the patient being treated. Intravenous injection of approximately 2–5 millicuries of the $Tc^{99m}$ calcium phytate colloid is followed by imaging of these organs a few minutes later. The present kit is unique in its simplicity and is readily employed by the clinician with maximum economy of time and effort.

EXAMPLE 1

Preparation of the Kit

Vial No. 1 containing a freeze-dried mixture of 10 mg. sodium phytate and 1 mg. of stannous chloride A solution is prepared by dissolving 40 g. of sodium phytate in 3200 ml. of sterile water and is then mixed with a mixture of 4 g. of stannous chloride dihydrate, 7 ml. of hydrochloric acid, and 200 ml. of sterile water. To the resulting solution is then added sufficient sterile water to make a total solution volume of 8000 ml. This solution is then subdivided into 2 ml. portions and filled into 10 cc. vials. The subdivided solutions are then aseptically freeze-dried to provide a readily-soluble, freeze-dried mixture of 10 mg. of sodium phytate and 1 mg. of stannous chloride in each vial and stored in a nitrogen atmosphere.

Vial No. 2 containing a buffered solution of calcium chloride

A solution is prepared of 50 g. calcium chloride dihydrate in 6500 ml. of sterile water. The solution is acidified with hydrochloric acid to a pH of 1.5. To the acidified solution is added 50 g. of potassium biphthalate and stirred until completely dissolved. A solution of 1 N sodium hydroxide is added until the solution has a pH of 3.2 ± 0.1. Additional sterile water is then added to bring the total volume of solution to 10,000 ml. The solution is then subdivided into 2.5 ml. portions and stored under nitrogen in 6 cc. vials; each vial containing in solution 12.5 mg. of calcium chloride (5 mg. ± 0.5 mg./ml.) and 12.5 mg. of potassium biphthalate (5.0 mg. ± 0.5 mg./ml.) and having a pH of 3.2 ± 0.1.

EXAMPLE 2

Use of Kit in Preparing Injectable Tc$^{99m}$ Colloid

Approximately 2-8 ml. of a sterile saline solution of from 20-50 millicuries of sodium pertechnate Tc$^{99m}$ (ordinarily about 25 millicuries) is aseptically added to the contents of Vial No. 1 of Example 1. The volume is adjusted to 8 ml. with sterile saline solution if desired. Then 2 ml. of the contents of Vial No. 2, containing calcium chloride buffer solution, is aseptically transferred to Vial No. 1 to give a total volume of 10 ml. The resulting mixture is then shaken to provide the final dosage form of injectable Tc$^{99m}$ calcium phytate colloid suitable as an agent for imaging liver, spleen, and bone marrow. This final form usually contains more than enough for one dose, ordinarily 3-5 doses containing from 2-5 millicuries/dose.

What is claimed is:

1. A kit for preparing Technetium 99m calcium phytate colloid injection which comprises in separate containers:
   a. a freeze-dried solid mixture of sodium phytate and stannous chloride; and
   b. a buffered aqueous solution of calcium chloride having a pH of between 2.7 and 3.7; wherein the said sodium phytate and the said calcium chloride are present in a ratio of approximately 1.0 to 1.0 by weight.

2. A kit in accordance with claim 1 wherein the pH of the calcium chloride is adjusted to between 3.1 and 3.3.

3. A kit in accordance with claim 2 wherein said freeze-dried mixture comprises 10 mg. of sodium phytate and 1 mg. of stannous chloride in the form of the dihydrate and said buffered aqueous solution comprises 12.5 mg. calcium chloride as the dihydrate and 12.5 mg. of potassium biphthalate dissolved in 2.5 ml. of normal saline solution.

4. In a process for preparing an injectable aqueous colloid of Technetium 99m calcium phytate, the improvement which comprises adding a buffered aqueous solution of a soluble calcium salt to a solution of sodium phytate complexed with reduced pertechnate ion.

5. A process according to claim 4 wherein the weight ratio of said phytate compound and said calcium chloride compound is 1 to 1.

* * * * *